United States Patent [19]

La Zare

[11] Patent Number: 4,509,836
[45] Date of Patent: Apr. 9, 1985

[54] MULTI FORMAT SHUTTERLESS MOTION PICTURE INSPECTION PROJECTOR

[76] Inventor: Howard T. La Zare, 10825 Fullbright Ave., Chatsworth, Calif. 91311

[21] Appl. No.: 462,990

[22] Filed: Feb. 1, 1983

[51] Int. Cl.³ ............ G03B 21/00; G03B 41/00; G03B 21/20
[52] U.S. Cl. .................................. 352/200; 352/79
[58] Field of Search ............ 352/200, 159, 79, 80

[56] References Cited

U.S. PATENT DOCUMENTS

| 1,786,917 | 12/1930 | Oehmichen | 352/159 |
| 2,473,625 | 6/1949 | Wheeler | 352/200 |
| 3,640,438 | 2/1972 | Morse et al. | 352/159 |

FOREIGN PATENT DOCUMENTS

| 364302 | 1/1932 | United Kingdom | 352/200 |

*Primary Examiner*—Monroe H. Hayes
*Attorney, Agent, or Firm*—Harlan P. Huebner

[57] ABSTRACT

A multi format shutterless inspection projector for motion picture film whereby the image projected will include a full frame heightwise and margin to margin widthwise to view the picture, sound track and sprocket holes. The apparatus includes condensing lenses, projection lenses and a shutterless film gate mounted therebetween. The illumination means is a strobe light and accompanying apparatus capable of exciting the lamp to micro-second flashes. In addition triggering means is on the projector to fire the strobe light apparatus and the triggering means is geared to the speed of travel of the film through the projector. Further, damping means are provided to control tension on the film as it enters the projector and also there are means to control the speed of the takeup reel motor.

11 Claims, 18 Drawing Figures

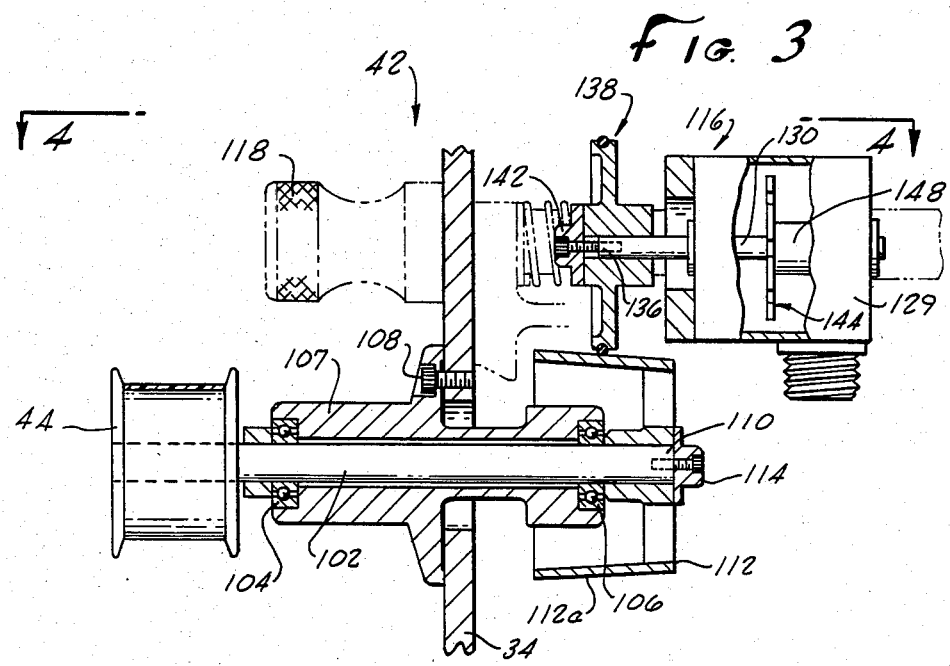
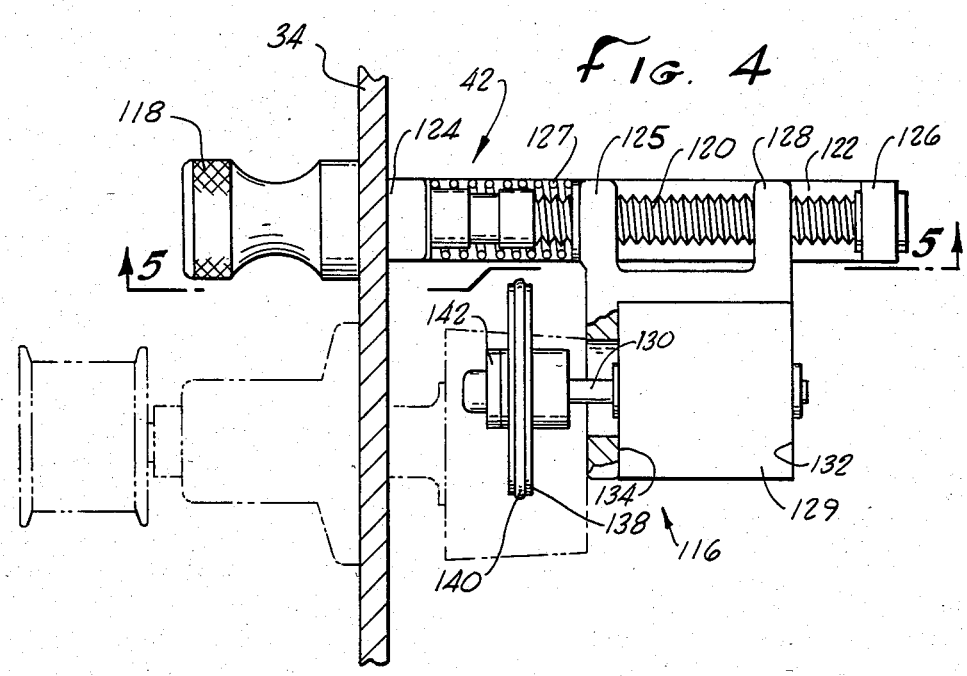

4,509,836

MULTI FORMAT SHUTTERLESS MOTION PICTURE INSPECTION PROJECTOR

BACKGROUND OF THE INVENTION

FIELD OF THE INVENTION

The present invention relates to a motion picture projector utilizing a high-intensity strobe light with controlled flash durations eliminating the need for frame shutter mechanism. The invention is capable of a multi format wherein different millimeters of film may follow one another without change of parts of the projector.

CROSS REFERENCE TO RELATED APPLICATION

This application is an improvement over co-pending application U.S. Ser. No. 422,030, filed Sept. 23, 1982 now abandoned.

DESCRIPTION OF THE PRIOR ART

In the field of inspection projectors it is necessary to inspect the motion picture film at the end of its development and processing to determine physical blemishes, abnormal color, sound track deficiencies, sprocket hole damage, etc.

Heretofore, means have been developed to endeavor to accomplish such inspection. However, the prior devices such as those disclosed in U.S. Pat. Nos. 4,113,367 and 4,126,386 are in off-line inspection rooms usually remote from the film developers and processors. Further, the mechanism of the above two patents are image stabilization system which utilize multifacet reflecting roof polygon scanners which require excessive and meticulous maintenance in order to assure minimum film damage. In addition such devices gather dust and wax from the newly developed film.

In 1940, U.S. Pat. No. 2,168,013 was issued directed to a motion picture apparatus more commonly known as a projector in which the shutter was eliminated. This projector drove the reel to pull the film through the projector past the lens but had the disadvantage of utilizing the drive means to also rotate a moveable contact member which in turn would activate a gaseous rectifier device. This particular structure possessed many other disadvantages not the least of which was the need again for excessive maintenance to achieve some form of correlation between film instantaneous frame immobility and illumination. Further, this device could not be used as an inspection projector to make a single film frame appear stationary for inspection purposes. In addition, a further disadvantage of U.S. Pat. No. 2,168,013 resides in the illumination of a frame for under fifty percent of the total time it is exposed. Finally, this prior art structure used sprocket wheels on the drive mechanism which increases the danger of damage to the film as it passes thereover. In addition the projector could not be used for a multiformat of motion picture film.

An additional patent of interest is U.S. Pat. No. 2,995,064 which relates to a shutterless projector. Again the principal is similar to U.S. Pat. No. 2,168,013 with the apparent ability to illuminate the frame for an increased period of time, but again employing a direct sprocket reel and light switch means. In this patent there is the disadvantage of a physically activated switching means which can malfunction. This would require excessive maintenance.

SUMMARY OF THE INVENTION

The present invention provides an improved shutterless projector particularly adapted for the inspection of motion picture film as it exits from the drying cabinet of developing and processing apparatus. This enables the film to be viewed before take-up and prompt corrective measures can be taken if any printing or processing problem occurs.

In addition, the inspection projector is capable of being an off-line projector where it is not adjacent a drying cabinet but independent such as in a separate film inspection room.

Another advantage is to provide an inspection projection capable of passing film of different formats past the lens for inspection. In other words footage of 35 mm film may be followed by footage of 16 mm film being sliced thereto and no additional equipment and modifications are necessary save a slight adjustment for pitch differences.

Another advantage of the present projector is the capability of passing film at a rapid rate of speed and still render crisp, bright images.

Another advantage of the present invention is that there is no shutter nor does it have any spring tension on the film gate all of which prevent damage to the film.

In addition the projector of this invention possesses the advantage of no dowser or intermittent movement of the film in the stop motion effect of the image on the screen.

Another object and advantage of the invention is that the film drive is supplied by a take-up reel and drive means other than in the projector.

A further advantage of the invention is to provide apparatus on the projector to regulate the flash rate of the strobe light all dependant upon the speed of the film traveling through the projector.

A still further advantage of the present invention is the use of rollers to guide the film through the film gate of the projector which eliminate wear and tear to the sprocket holes on the marginal edges of the film caused by conventional sprocket wheels.

These and other advantages will become apparent as to the organization and manner of operation of the projector, together with further objects and advantages thereof by reference to the following description, taken in connection with the accompanying drawings.

BRIEF DESCRIPTION OF THE DRAWINGS

FIG. 3 is a front elevational view of the film roller assembly and the variable transmission trigger units taken on line 3—3 of FIG. 2;

FIG. 4 is a top view taken on line 4—4 of FIG. 3;

BRIEF DESCRIPTION OF THE PREFERRED EMBODIMENT

Figure 1:
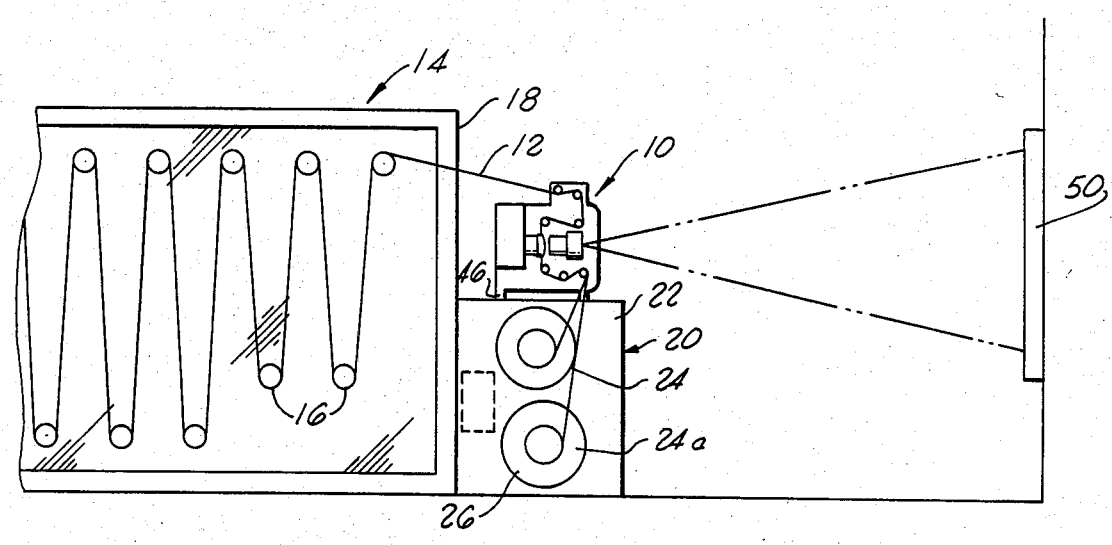
FIG. 1 is an environmental view of one location and use of the projector comprising the present invention.

In FIG. 1 there is illustrated a shutterless motion picture film projector generally designated 10 particularly adapted for visual inspection of motion picture film 12 after it has been developed, processed and dried. In the preferred embodiment the projector 10 known as an inspection projector is installed at the end of a conventional film drying tank or dry box 14. The tank 14 may include a plurality of floatable rollers or elevators 16 over which the film 12 is treaded after it leaves the processing section (not Shown).

The processing equipment including drying tank 14 is known as endless because a number of reels of undeveloped film may be spliced in end-to-end relationship, pass for processing and exit out the drying tank 14. The rollers 16 are "floating" so that the film take up station maybe stopped for roll removal or change over while the floating rollers accommodate the continuously moving film.

At the end 18 of tank 14 there is secured a table or support 29 having at least one side 22 to which is mounted at least one film take-up drive means 24a so the movement of the film from the drying tank 14 is not seriously curtailed for a period of time greater than can be accommodated by the floating rollers 16.

The film take-up means 24 and 24a includes a reel or reels 26 mounted thereon and are connected to a motor or motors (not shown) within the table 20 behind the side 22.

Figure 14:
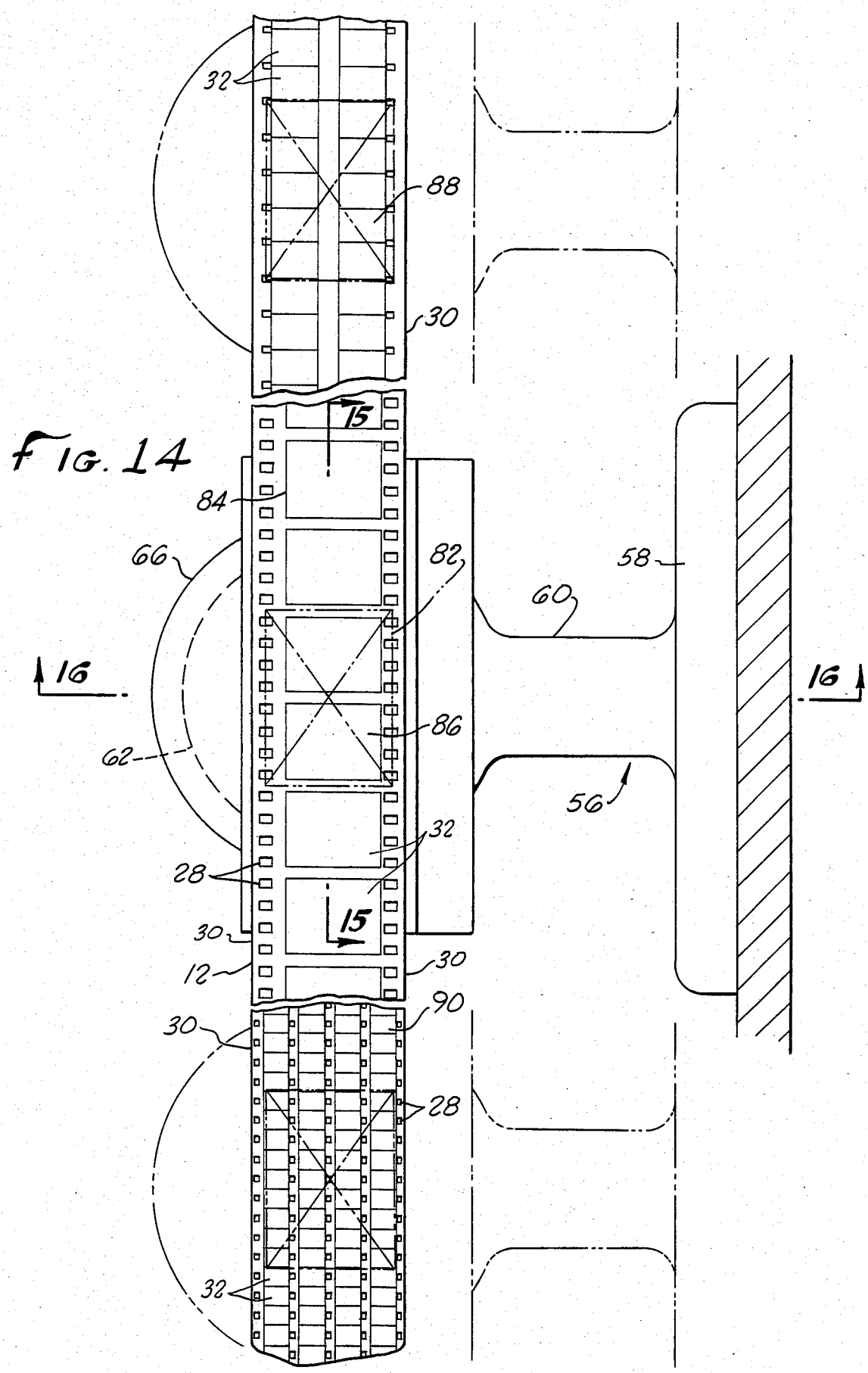
FIG. 14 is a front view of various film formats to illustrate the multi-format capability of the projector.

The film 12 is conventional motion picture film either of the usual 35 mm, 35/32 mm, 16 mm, or 8 mm variety. As best seen in FIG. 14 the film 12 includes sprocket holes 28 on both marginal edges 30 there are sequential picture frames 31. Generally speaking with regard to 35 mm film, the center film in FIG. 14, there are four sprocket holes on each side of each frame 32. The number for 35/32 mm and 8 mm will vary as can be seen in the drawing FIG. 14.

Mounted on the table 20 is the projector 10. Generally the projector 10 includes a cabinet 34, lamphouse 36, condensing lens 38, projecting lens 40, and film gate guide roller 44 and 44a, all mounted on the cabinet 34.

The housing or cabinet 34 includes a plurality of feet 46 which may be adjustable to assure the centering and leveling of the projected film 12 through the projecting lens 40 to screen 50.

The condensing lenses 38 are conventional in nature and projecting lens 40 can be produced to match the curvature of the gate. The projecting lens 40 includes a threaded screw or clamp means 52 which can shift the lens 40 to focus the projected image on the inspection screen 50.

Figure 15:
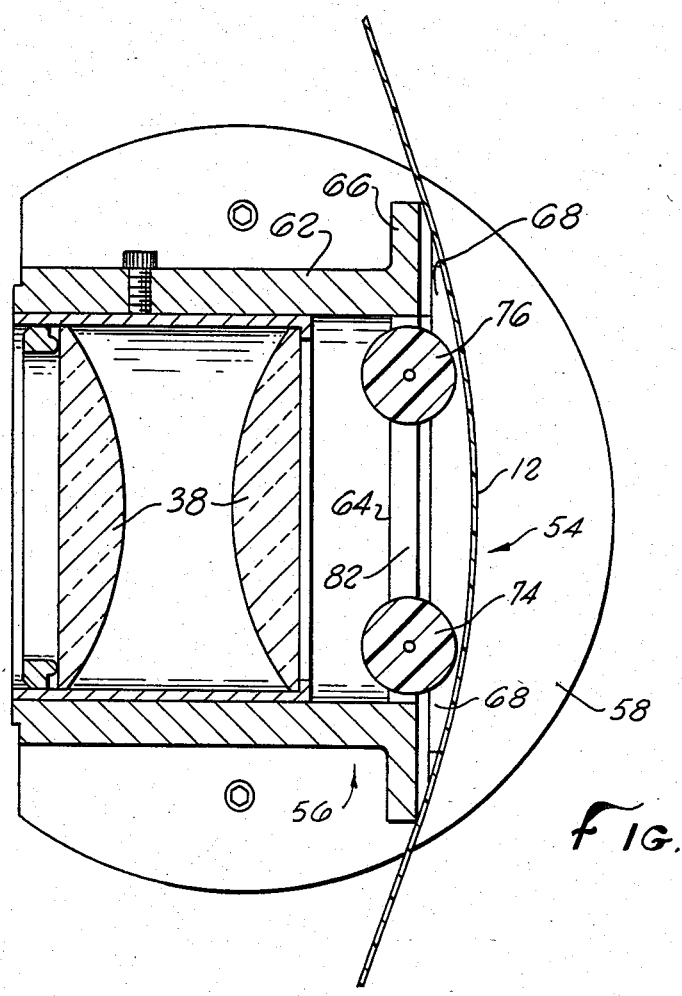
FIG. 15 is a side elevational view in section taken on line 15—15 of FIG. 14.
Figure 16:
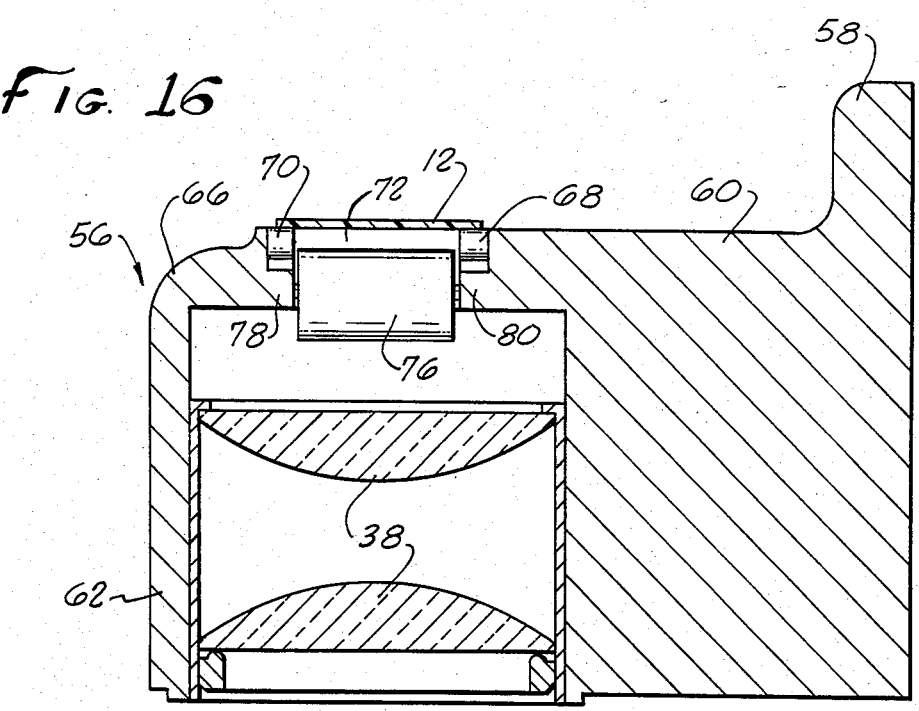
FIG. 16 is top view, partially in section taken on line 16—16 of FIG. 14.

Positioned between the condensing lenses 38 and projecting lens 40 is a shutterless film gate 54 (see FIGS. 15 and 16). The gate 54 is mounted on a gate and lens holder generally designated 56 with a base 58 mounted on the cabinet 34 and including a neck 60 extending to a lens housing 62. The housing 62 at the front end 64 includes the film gate means 54. The front 64 includes an annular flange 66. Mounted in the flange are a pair of curved spaced apart parallel rails 68 and 70 upon which the film 12 may ride. Mounted in the vertical opening 72 formed between the rails 68 and 70 in the gate means 54 are a pair of backup rollers 74 and 76 to prevent the film 12 from moving off the rails 68 and 70 if high tension should occur. The rollers 74 and 76 are journaled into the walls 78 and 80 for rotation. As can be seen from FIG. 15 the light will come through lens 38 and an aparature or gate 82 between the rollers 74 and 76 and pass through the film frames 32 as they pass by the gate 82. By having the rails 68 and 70 curved a wrap may be created in the film 12 thereby providing a self-support and flatness for the film across the aperature.

The aperature or gate 82 corresponds to the height of a film frame 32 and has a width corresponding to the entire width of the film 12 to the exterior marginal edges thereof. In this way not only will the picture in the frames 32 be viewable but also the sound track which is usually placed on the film between the edge 84 of the film and the sprocket holes 28 on one side of the film. In addition the sprocket holes 28 on both sides too may be viewed to determine whether they are damaged or broken.

It should be noted that one of the important features of this invention is to inspect the film frames of the various widths of film such as 35 mm, 86 (see FIG. 14), 35/32 mm 88 and Quad 8 mm, 90. In other words 35 mm, 35/32 mm, and Quad 8 mm film can and are all run on film 12 with a common width. The only difference resides in the number of frames 32 instantaneously illuminated on the screen 50. In the case of 35 mm 86, as can be seen in FIG. 14, two frames can interfit in front of the gate or aperature 82. In the case of 35/32 mm five full frames in height (10 total) can interfit in front of the gate. With regard to Quad 8 mm nine full frames 32 in height (36 total) are viewable. Film of different widths can be accommodated by inserting appropriately spaced supporting rails and adding appropriate rollers.

Thus in the present invention it is no longer necessary to only run for viewing a film of a single dimension and then change equipment such as gates and sprocket wheels. With the present invention a length of 35 mm can be spliced to Quad 8 mm film or 35/32 mm film or visa-versa. In this way the film inspection process can be continuous and encompass the multi formats of film.

In order to accomplish the viewing of differing formats of film, apparatus is necessary to slow up or speed up the triggering rate in relationship to the film traveled as it passes to gate 82. To this end there is the film triggering or electronic-mechanical compensation control means 42 which will subsequently be discussed in detail.

Figure 17:
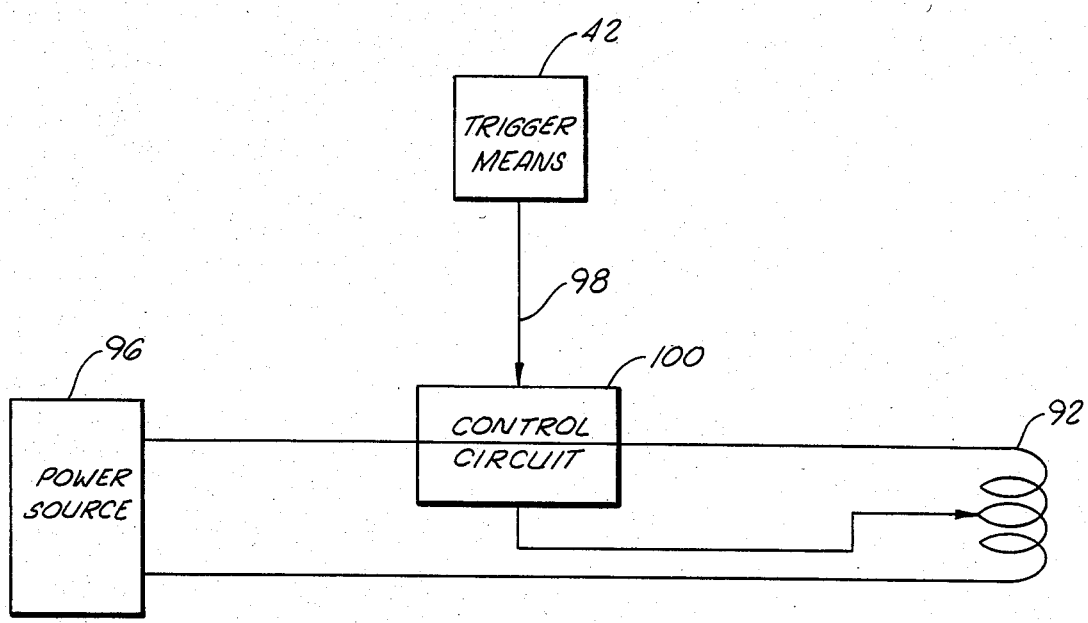
FIG. 17 is a schematic of the electrical circuit to control the pulsation of the illumination means.
Figure 18:
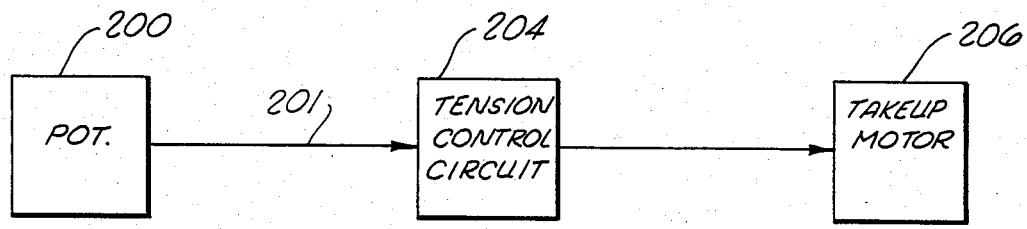
FIG. 18, is a schematic of the motion damping and tension sensor assembly of FIGS. 6 and 7.

Turning now to the lamp housing 36 there is illustrated a conventional strobe light 92 with a reflector 94 mounted therebehind. The strobe 92 is subject to milli or fraction of second activation and illumination through conventional condensors and other apparatus not shown. Both the strobe light 92 and reflector 94 are in line with the lens 38 and film gate. There is also shown for illustration power source 96 (FIG. 17) which can excite the light 92 through which firing or flashing can be controlled through the trigger means 42. The live line 98 (best seen in FIGS. 13 and 17) carries the impulses to the control circuit 100 which in turn controls the power and lamp 92 and also triggers the lamp 92. The control circuit 100 also holds the lamp on until the power is turned off.

It has been found that with periodic firing at a rapid rate of high intensity strobe lamp the need for a traditional film gate with shutter is unnecessary. By keying the firing of the strobe 92 to the speed of the film through the gate 82 the projected image will be of a stop motion effect without flutter or dowser, yet continue as a motion picture film to be viewed by the operator or technician.

Figure 8:
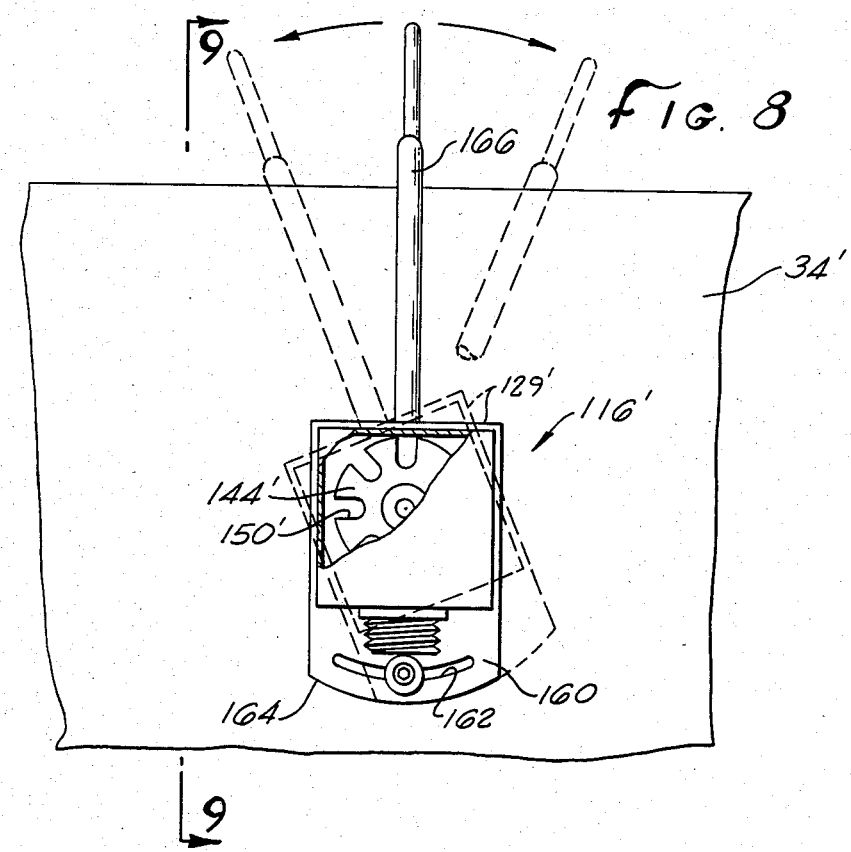
FIG. 8 is a side elevational view of a framing device for use with a single formated sprocket system.
Figure 9:
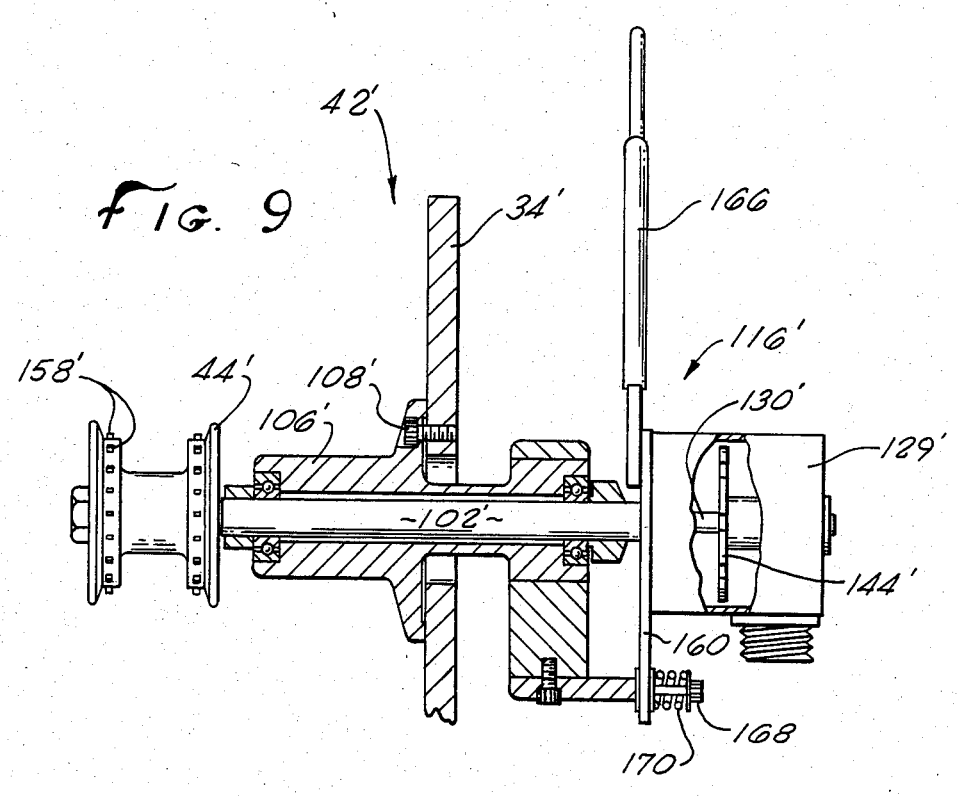
FIG. 9 is a front elevational view taken on line 9—9 of the FIG. 8 device and shows the use of the device with a film sprocket wheel.
Figure 11:
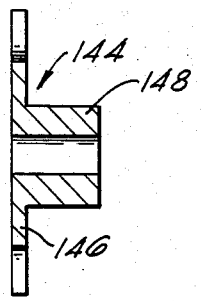
FIG. 11 is a sectional view taken on line 11—11 of FIG. 10.

Now attention is directed to the electronic-mechanical compensation control means 42 best view in FIGS. 3 through 5, and 11 through 13. A modified means 42' is illustrated in FIGS. 8 and 9.

The control means 42 includes the film gate roller 44 mounted on a rotatable shaft 102 which is journaled in bearings 104 and 106 in turn mounted in a roller bearing housing 107. The bearing housing 107 is mounted to the cabinet 34 by means of screw 108. Mounted on the end 110 of the shaft 102 is a frusto conical speed control roller 112 which is held thereon by retainer 114.

Mounted above the roller 112 as a part of the control means 42 is trigger assembly 116. There is a finger knob 118 projecting outside of the cabinet 34. The knob 118 passes through an opening (not shown) in the cabinet 34 and is joined to a lead screw 120. The lead screw 120 in turn is mounted in a lead screw support 122 (see FIG. 5) which in turn is secured to the cabinet 34. The screw 120 passes through a pair of spaced apart threaded extensions 124 and 126. A tension spring 27 may be used to assure that the screw 120 will not rotate or move on its own.

Suspended from the lead screw 120 are a pair of mounting brackets 125 and 128 whichin turn are secured to an encoder housing 129. The brackets are threaded to receive the lead screw 120. Mounted horizontally in the housing 129 is a trigger roller shaft 130 journalled in the rear wall 132 and forward wall 134 of the housing 129. The shaft 130 projects out of the housing 129 toward the cabinet 34 and mounted on the exterior end 136 of shaft 130 is a trigger roller 138. A friction rubber rim 140 is preferably placed on the roller. A retainer cap 142 holds the roller on the shaft 130.

Figure 10:
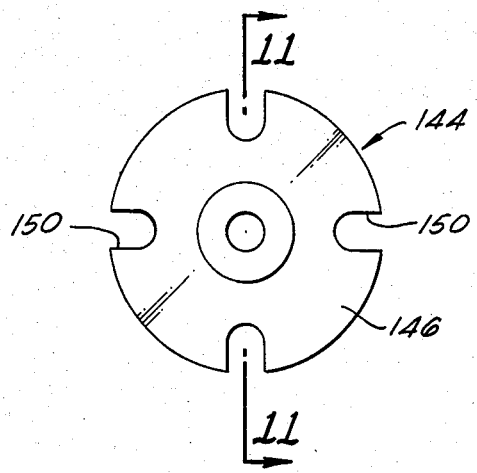
FIG. 10 is a front view of a chopper disc to control pulsations of the illumination means.
Figure 12:
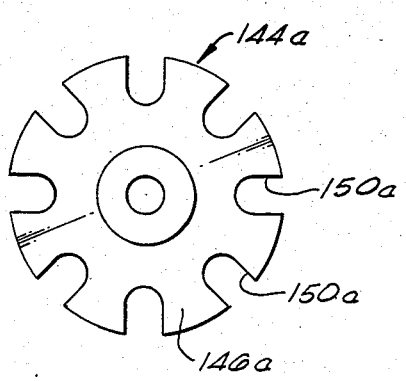
FIG. 12 is a front view of a modified chopper disc similar to FIG. 10.

Also mounted on the shaft 130 is an encoder disc 144 which includes a flat plate 146 and a mounting hub 148 for the shaft 130. The disc around its periphery has a series of cutouts 150 which in the case of the disc in FIG. 10 are arranged at 90° increments around the disc 144. The disc 144a in FIG. 12 has cutouts 150a arranged around the periphery at 45° increments.

Figure 13:
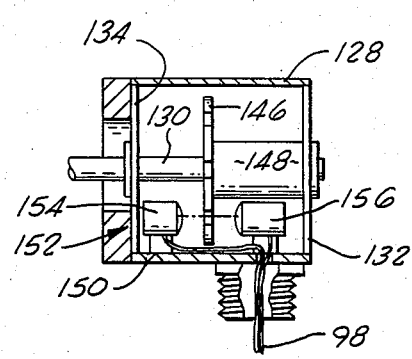
FIG. 13 is a detailed assembly of the chopper disc in position to control pulsation of the illumination means.

Mounted on the floor 150 of the housing is a light triggering means 152 which may comprise a photo cell 154 and light-source 156 which are aligned one on each side of the encoder disc 144 as best seen in FIG. 13.

In operation, depending on the type of film passing over the roller 44 the knob 118 may be rotated to move the mounting brackets 125 and 128 and in turn the housing 129 and trigger roller 138 back and forth on the lead screw 120. As the rubber rim 140 of the roller 138 engages the frusto conical speed roller 112 along its inclided surface the speed of the roller 44 can be imparted to the roller 138 and in turn to the encoder disc 144. With the light triggering means 152 constantly on when the cutouts 150 or 150a pass through the beam of the photo cell 154 it will remain on and pass an electrical impulse signal through line 98 to the control circuit 100 whereby the strobe light is illuminated.

Thus where film travels through the projector 10 at the rate of 300 feet per minute or greater the four cutout disc 150 is sufficient. This spacing will equal a lamp duration for 2 35 mm frames. In the event a slower film speed is desired then the disc 144a is used. By adjusting the knob 118 the speed of the disc 144 can be controlled and changed so that the viewing of the film on the inspection screen 50 will be without flicker. This is of course caused because as the roller 138 moves on the inclined surface 112a of the roller 112 the speed of the roller 138 can be increased or decreased relative to the speed of roller 44.

Turning now to the modified trigger means 42' of FIGS. 8 and 9 this particular assembly is useful if the projector is to only receive one film format such as only 35 mm film. Here the roller 44' is a sprocket roller with sprockets 158' to engage the sprocket holes 28 of film 12 (not shown). The difference of the means 42' resides in the trigger assembly 116'. Here the shaft 102 extends rearwardly through the front wall of the encoder housing 129. Secured to the shaft 102' is trigger roller shaft 130' to which is mounted on encoder disc 144'.

Secured to the front of the housing is a shaft encoder swivel plate 160. The plate includes an arcuate cutout 162 adjacent the bottom 164 of the plate 160. Mounted on the plate 160 and extending upward and out of the cabinet 34' is a swivel rod 166. The swivel plate 160 is held against unwanted movement by means of a set pin 168 and tension spring 170.

In operation, when the projector is to be used only for film of one format the rotation ratio of the encoder disc 144' is not changed. It will rotate at the speed of the film roller 44' as it is directly connected thereto by shaft 102'. However, by moving the swivel rod 166 to positions as shown in FIG. 8 the encoder housing 129' may be rotated about the disc 144'. In this way the photo cell or other variable speed control sensor means 152 will be shifted so the impulse or firing point passing through outlets 150' can be varied. In this way proper excitement of the strobe 92 may be manually adjusted by the swivel rod 166.

While the preferred film triggering means 42 is that described above, it must be recognized that other forms of triggering to excite the strobe 92 may be provided. The sprocket holes of the film passing the gate 82 can be utilized as a counter. In other words the passing of the film 12 at a specific point can by appropriate in line means activate the power source 96.

Figure 2:
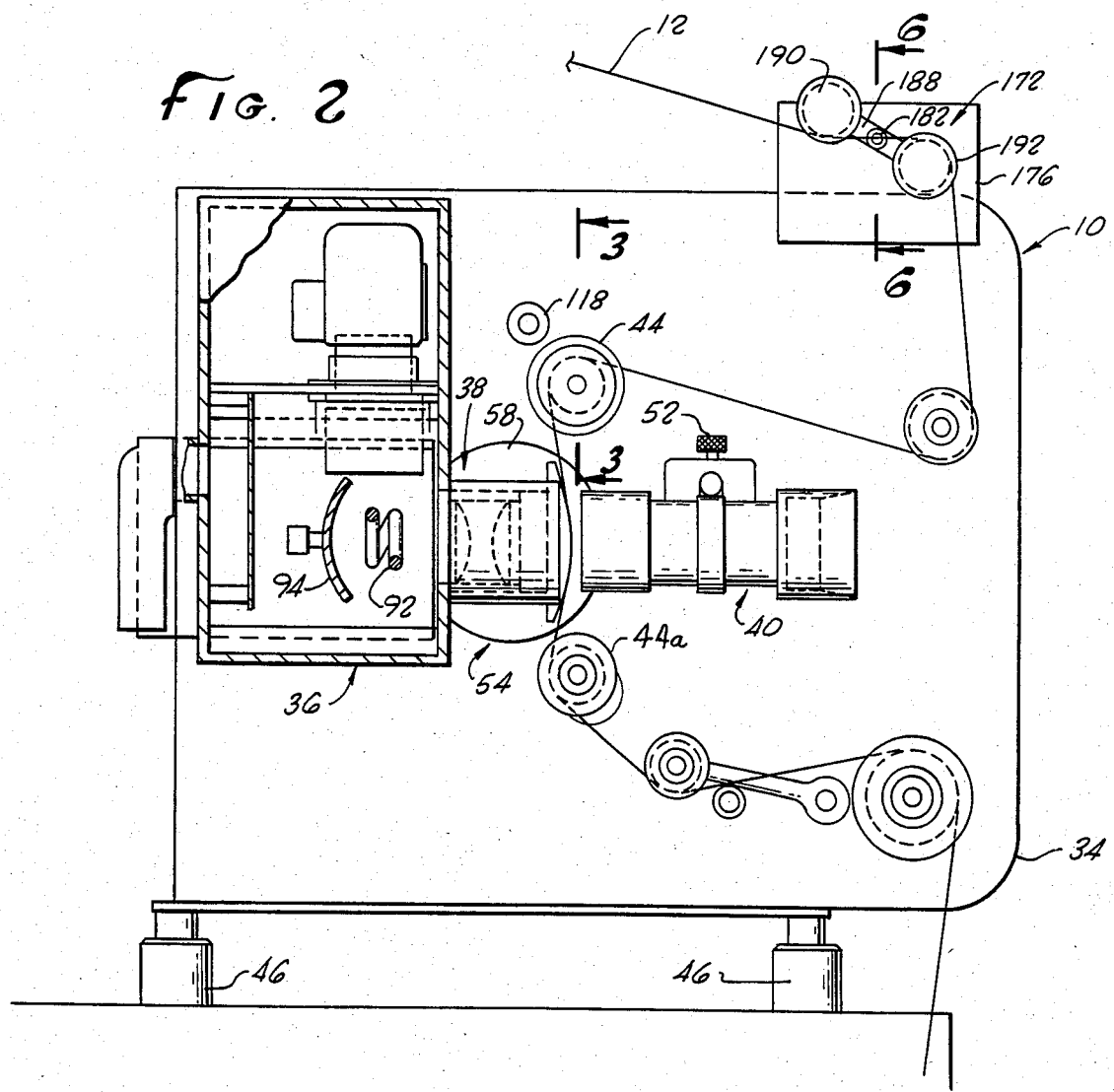
FIG. 2 is a side elevational view of the shutterless projector of the present invention with film threaded therethrough.
Figure 5:
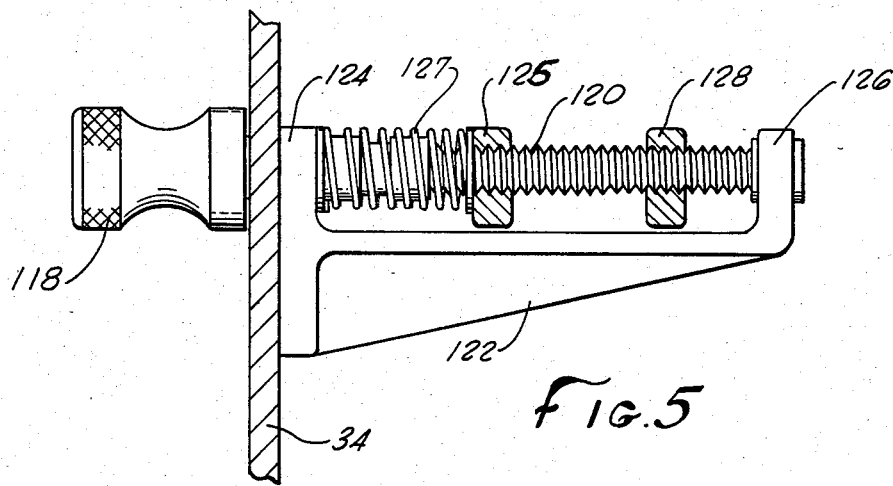
FIG. 5 is a view taken on line 5—5 of FIG. 5, showing the control knob structure of the apparatus in FIG. 3.
Figure 6:
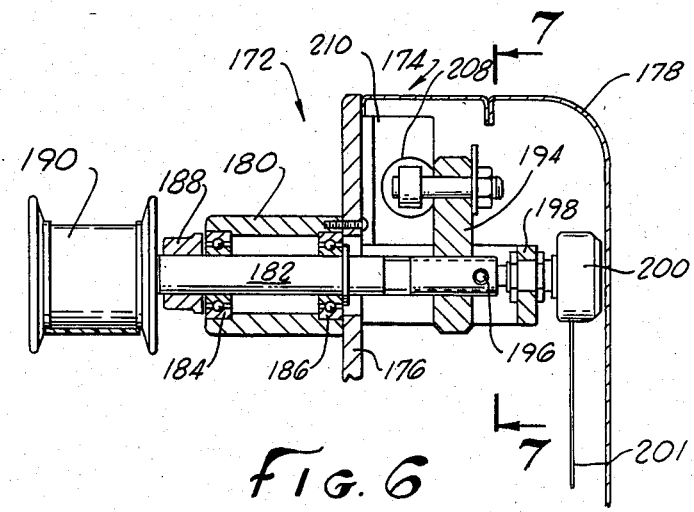
FIG. 6 is a front elevational view taken on line 6—6 of FIG. 2 illustrating a motion damping and tension sensor assembly, for assisting in controlling the travel of the film.
Figure 7:
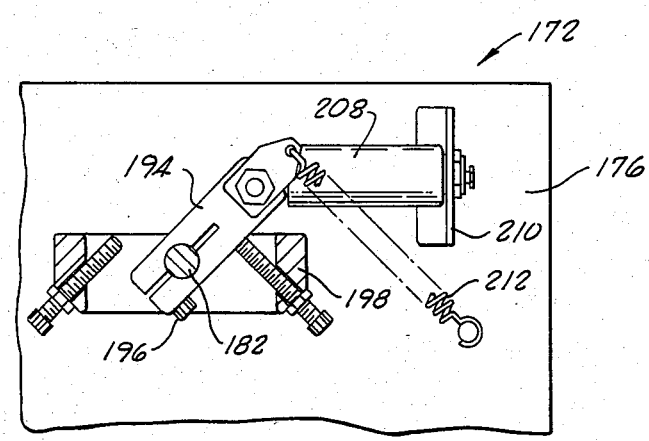
FIG. 7 is a view taken on line 7—7 of FIG. 6 of additional details of the dampener rocker arm.

In FIGS. 2, 6 and 7 details of the motion damping systems 172 are illustrated. The purpose of this system is to achieve constant tension and smooth motion of the film 12 as it emerges from the dry box 14 and prevent flutter as the film passes the film gate 54.

Mounted on the cabinet 34 is motion damper housing 174 having a front wall 176 and a cover 178. Secured to the front wall 176 is a bearinghousing 180. A shaft 182 extends through bearings 184 and 186 projecting outwardly and inwardly of the wall 176. Journalled on the forward end of the shaft 182 is a dancer rocker arm 188. The dancer rocker arm 188 includes a pair of smooth sprocketless rollers 190 and 192 journalled on opposite ends of the arm. The rollers 190 and 192 are to receive the film 12 passing under roller 190 and over roller 192, see FIG. 1 for the threading of the film.

The inward end of shaft 182 extends through wall 176 through piston arm 194. The arm 194 is secured to the shaft 182 by means of set screw 196. At the point of connection with the arm 194 the shaft 182 is preferably reduced in diameter and passes through a rheostat mountingbracket 198 to a potentiometer 200, see FIG. 6. A lead wire 201 runs from the potentiometer 200 to a tension control circuit 204, not show in detail which in turn runs to a takeup motor 206, not shown in detail behind the takeup reel means 24.

The piston arm 194 at the end opposite that connected to shaft 182 is connected to a dash pot 208 fitted to the front wall 176 by bracket 210. A tension spring 212 is provided to maintain the pivot arm 194.

In operation, the potentiometer 200 is activated by the tension of the film causing shaft 182 to rotate. In this manner the rocker arm 188 will pivot up or down so that the rollers 190 and 192 are raised or lowered about the shaft 182. Therefore, the tension of the film will be reflected and corrected in the motor speed of the takeup motor 206 resulting in constant tension of the film as it passed through projector 10 to the takeup system.

The dash pot 208 will assist in preventing vibration and may be of any conventional type.

While the above embodiments have been disclosed as the best mode presently contemplated by the inventors, it should be realized that these examples should not be interpreted as limiting, because artisans skilled in this field, once given the present teachings can vary fron these specific embodiments. Accordingly, the scope of the present invention should be determined solely from the claims.

I claim:

1. A multi format shutterless inspection projector for motion picture film said projection being capable of rapid continuous projection of entire film frames from margin to margin upon a screen for visual inspection thereof across the entire frame of said film after it is developed and processed to inspect for color, quality and damage including:
    a projector housing;
    lens means mounted on said housing including light condensing lenses and projecting lenses to project said film frames;
    a shutterless film gate interposed between said condensing lenses and said projecting lenses, said gate includes two spaced apart smooth rails forming a film frame aperture therebetween whereby film for inspection will be guided over said rails past said aperture for projection and said space between said rails is of such width as to extend to the marginal edges of each of the said film;
    a strobe light means on said housing behind and in line with said condensing lenses and said projecting lenses adapted to be activated and deactivated in fractions of seconds to project said frames;
    multi format trigger roller means on said housing which is adjustable during the continuous operation of said projector to activate the frequency of firing said strobe light means as each film frame moves past said aperture dependent upon what format of film is passing said aperture, whereby said frames will each be illuminated and projected on said screen for viewing yet maintaining the motion created by sequentially viewing a series of frames;
    said multi format trigger roller means includes a roller mounted on said housing above said shutterless film gate over which film will pass and rotate said roller, a trigger roller assembly associated with said roller and rotatable through rotation of said roller; and
    manual means connected to said trigger roller assembly to change the rotational speed of said trigger roller assembly from said roller dependent upon what film format is passing said aperture;
    a power source and control circuit forming a part of said strobe light means and said source and control circuit controlled by said trigger means, and
    film take up means separate from said projector adapted to pull said film through said film gate to a storage film reel.

2. A multi format shutterless inspection projection as defined in claim 1 wherein the roller is sprocketless.

3. A multi format shutterless inspection projector as defined in claim 1 wherein said roller includes a shaft projecting into said housing and terminating in a frusto conical speed roller with a tapered annular wall.

4. A multi format shutterless inspection projector as defined in claim 3 wherein said trigger roller assembly includes:
    a trigger roller engaging said tapered annular wall;
    an encoder disc rotatably mounted on a shaft projecting from said trigger roller;
    a housing surrounding said encoder disc and portion of said trigger shaft;
    light means within said housing projecting a beam; and
    said encoder disc positioning to intercept said beam and due to its peripheral configuration capable of intermittanty pulsating said beam by breaking the same upon its rotation, and said light means passing said pulsations to said control circuit.

5. A multi format shutterless inspection projector as defined in claim 4 wherein said encoder disc has a plurality of peripheral cut outs annually spaced around said disc.

6. A multi format shutterless inspection projector as defined in claim 2 wherein said manual means is a finger knob.

7. A multi format shutterless inspection projector as defined in claim 1 wherein said roller contains sprockets in the event a single format film is to be used for inspection for a relative length of time.

8. A multi format shutterless inspection projector as defined in claim 7 wherein said roller is connected to said trigger roller assembly.

9. A multi format shutterless inspection projector as defined in claim 7 wherein the trigger roller assembly includes:
    an encoder disc directly connected to said roller through a shaft;

a housing surrounding said encoder disc and a portion of said shaft, yet not connected thereto and capable of independent pivotal movement about said shaft;

a control handle projecting from said projector housing connected to said housing for pivoting said housing; and light means within said housing projecting a beam and capable of having said disc intercept said beam and creating a pulsation which is passed to said control circuit.

10. A multi format shutterless inspection projector as defined in claim 3 which includes a dash pot connected to said dancer rocker arm to prevent fluttering of said film frames as they pass said film aperture.

11. A multi format shutterless inspection projector for motion picture film said projection being capable of rapid continuous projection of entire film frames from margin to margin upon a screen for visual inspection thereof across the entire frame of said film after it is developed and processed to inspect for color, quality and damage including:

a projector housing:

lens means mounted on said housing including light condensing lenses and projecting lenses to project said film frames;

a shutterless film gate interposed between said condensing lenses and said projecting lenses, said gate includes two spaced apart smooth rails forming a film frame aperture therebetween whereby film for inspection will be guided over said rails past said aperture for projection and said space between said rails is of such width as to extend to the marginal edges of each of the said film;

a strobe light means on said housing behind and in line with said condensing lenses and said projecting lenses adapted to be activated and deactivated in fraction of seconds to project said frames;

trigger means on said housing to activate the frequency of firing said strobe light means as each film frame moves past said aperture dependent upon what format of film is passing said aperture, whereby said frames will each be illuminated and projected on said screen for viewing yet maintaining the motion created by sequentially viewing a series of frames;

a power source and control circuit forming a part of said strobe light means and said source and control circuit controlled by said trigger means, and film take up means separate from said projector adapted to pull said film through said film gate to a storage film reel;

said projector positioned adjacent the drying tank of a continuous film developer and processor and including a motion dampening system for controlling the tension of of the film as it emerges therefrom;

said motion dampening system includes a dancer rocker arm with a part of rollers for receiving and guiding incoming film; and a potentiometer associated with said dancer rocker arm connected to said control circuit and to said take up means to control the rocking of said arm and the constant tension of said film dependent upon the control circuit command.

* * * * *